(12) United States Patent
Castro et al.

(10) Patent No.: US 9,080,153 B2
(45) Date of Patent: Jul. 14, 2015

(54) TREATMENT METHOD FOR MESENCHYMAL STEM CELLS AND THEIR APPLICATION AS A TREATMENT OF OXIDATIVE STRESS RELATED DISEASES

(75) Inventors: Maria Begona Castro, Leioa (ES); Javier Diez Garcia, Bilbao (ES)

(73) Assignee: HISTOCELL S.L., Derio (ES)

( * ) Notice: Subject to any disclaimer, the term of this patent is extended or adjusted under 35 U.S.C. 154(b) by 0 days.

(21) Appl. No.: 14/131,049

(22) PCT Filed: Jul. 6, 2011

(86) PCT No.: PCT/ES2011/070489
§ 371 (c)(1),
(2), (4) Date: Jan. 6, 2014

(87) PCT Pub. No.: WO2013/004859
PCT Pub. Date: Jan. 10, 2013

(65) Prior Publication Data
US 2014/0154221 A1    Jun. 5, 2014

(51) Int. Cl.
*A61K 35/12* (2006.01)
*C12N 5/0775* (2010.01)
*A61K 35/28* (2015.01)

(52) U.S. Cl.
CPC ............... *C12N 5/0667* (2013.01); *A61K 35/28* (2013.01); *C12N 2500/02* (2013.01)

(58) Field of Classification Search
USPC .......................................... 424/93.7; 435/325
See application file for complete search history.

(56) References Cited

U.S. PATENT DOCUMENTS

2007/0077649 A1* 4/2007 Sammak et al. .............. 435/325
2009/0274770 A1* 11/2009 Gammelsaeter et al. ..... 424/581
2013/0164267 A1* 6/2013 Lin et al. ...................... 424/93.7

FOREIGN PATENT DOCUMENTS

WO    2004/044142 A2    5/2004
WO    2009/152384 A1    12/2009
WO    2010/011131 A1    1/2010

OTHER PUBLICATIONS

Kim W. et al. Evidence Supporting Antioxidant Action of Adipose Derived Stem Cells. J of Dermatological Science 49:133-142, 2008.*
Anita Brandl et al., "Oxidative stress induces senescence in human mesenchymal stem cells", Experimental Cell Research 2011, pp. 1541-1547, vol. 317, No. 11.
Gerhard Thomas Laschober et al., "Leptin receptor/CD295 is upregulated on primary human mesenchymal stem cells of advancing biological age and distinctly marks the subpopulation of dying cells", Experimental Gerontology 2009, pp. 57-62, vol. 44, No. 1-2.
Ji-Soo Kim et al., "Proteomic and metabolomic analysis of $H_2O_2$-induced premature senescent human mesenchymal stem cells", Experimental Gerontology 2011, pp. 500-510, vol. 46, No. 6.
International Search Report for PCT/ES2011/070489 dated Mar. 21, 2012.

* cited by examiner

*Primary Examiner* — Ralph Gitomer
(74) *Attorney, Agent, or Firm* — Sughrue Mion, PLLC (57) ABSTRACT

The present invention relates to a method of treatment of mesenchymal stem cells, preferably from adipose origin, comprising mainly two stages, firstly the collection and isolation of mesenchymal stem cells, and secondly, a period of growth and specific treatment of cells in a conditioning or treatment medium with an oxidizing agent. The invention also comprises the cells obtained directly through the method and its use in treating diseases caused by or associated with oxidative stress.

20 Claims, 6 Drawing Sheets

| Genes | β-actin |
|---|---|
| Rate HC016/hAMSC | 1,6 |

C

D

| Genes | IGF-1 |
|---|---|
| Rate HC016/hAMSC | 1,6 |

TREATMENT METHOD FOR MESENCHYMAL STEM CELLS AND THEIR APPLICATION AS A TREATMENT OF OXIDATIVE STRESS RELATED DISEASES

CROSS REFERENCE TO RELATED APPLICATIONS

This application is a National Stage application filed under Rule 371 based upon PCT/ES2011/070489 filed Jul. 6, 2011.

TECHNICAL ASPECT OF THE INVENTION

The present invention relates to a treatment method for mesenchymal stem cells, cells directly obtained through this method and their use in the care of diseases caused by or related to oxidative stress.

BACKGROUND OF THE INVENTION

Stem cell potential relies on their capacity to differentiate in defined cell types and integrate into corresponding tissues and organs. Another profitable feature of stem cells is their paracrine release of cytokines, interleukines, thrphic factors and growth factors.

Current research and clinical trials are being designed to probe the therapeutic effect of stem cells in several pathologies, and there is an increasing demand for stem cell-based therapies.

Certain degenerative diseases of the respiratory system, cardiovascular system, immune system, endocrine system/function, central and peripheral nervous systems, spinal cord injury, ischemia/reperfusion injury and demyelinating diseases have an inflammatory component mediated by reactive oxygen species (ROS) named oxidative stress.

Reactive oxygen species, principally superoxide anion radical ($O_2^-$) and its dismutation product $H_2O_2$, are natural waste subproducts in mitochondria of cells where respiratory chain takes part, a phenomenon vital for cell life due to its function in energy molecule (ATP) generation.

Mitochondria are the most redox-active compartment of mammalian cells, accounting for more than 90% of electron transfer to $O_2$ as the terminal electron acceptor. The predominant electron transfer occurs through a central redox circuit which uses the potential energy available from oxidation of various metabolic substrates (e.g., pyruvate, fatty acids) to generate ATP. Regulation of this process is central to cell function because cells must produce ATP while at the same time maintain an appropriate homeostasis in terms of supply of non-essential amino acids, eliminate excess amino acids, supply glucose and interconvert energy precursors to allow for long-term energy supply in the face of variable and intermittent food intake. Part of the regulation appears to occur through a continuous low rate of ROS generation and molecular sensors. The associated redox circuitry for this regulation, although poorly defined is known to require a specialized redox environment.

Under excessive oxidative stress, simultaneous collapse of the mitochondrial ATP-generation potential and a transient increase in ROS generation by the electron transfer chain, can result in mitochondrial release of ROS to cytosol. This can trigger "ROS-induced ROS release" in neighboring mitochondria. Thus, although a low rate of ROS generation is a normal process in mitochondria, disruption of electron flow with excessive ROS generation can result in senescence, apoptosis and cell death. Go and Jones, 2008. Redox compartmentalization in eukaryotic cells. Biochimica et Biophysica Acta 1780 (1273-1290); Zorov, Juhaszova and Sollott. 2006. Mitochondrial ROS-induced ROS release: an update and review. Biochim Biophys Acta 1757 (509-517).

Indeed, these processes are directly relevant to mitochondrial oxidative stress-related diseases such as Parkinson's disease, Friedrich's ataxia, Huntington disease and diabetes. Go and Jones, 2008. Redox compartmentalization in eukaryotic cells. Biochimica et Biophysica Acta 1780 (1273-1290); Dringen, Gutterer and Hirrlinger, 2000. Glutathione metabolism in brain. Metabolic interaction between astrocytes and neurons in the defense against reactive oxygen species. Eur J Biochem 267 (4912-4916); Chinta and Andersen, 2008. Redox imbalance in Parkinson's disease. Biochimica et Biophysica Acta 1780 (1362-1367); Cohen, 2000. Oxidative stress, mitochondrial respiration, and Parkinson's disease. Ann NY Acad Sci 899 (112-120); Lodi, Tonon, Calabrese and Schapira, 2006. Friedreich's ataxia: from disease mechanisms to therapeutic interventions. Antioxid Redox Signal 8 (438-443); McGill and Beal, 2006. PGC-1alpha, a new therapeutic target in Huntington's disease? Cell 127 (465-468); Donath, Ehses, Maedler, Schumann, Ellingsgaard, Eppler and Reinecke, 2005. Mechanisms of beta-cell death in type 2 diabetes. Diabetes 54 (Suppl 2) (S108-S113).

Peroxides, including hydrogen peroxide ($H_2O_2$), are one of the main reactive oxygen species (ROS) leading to oxidative stress. $H_2O_2$ is continuously generated by several enzymes (including superoxide dismutase, glucose oxidase, and monoamine oxidase) and must be degraded to prevent oxidative damage. The cytotoxic effect of $H_2O_2$ is thought to be caused by hydroxyl radicals generated from iron catalyzed reactions, causing subsequent damage to DNA, proteins and membrane lipids. $H_2O_2$ acts as a "suicide substrate" at high concentrations (>100 µM), leading to an irreversible inactivation of catalase. Hyslop, Zhang, Pearson y Phebus, 1995. Measurement of striatal $H_2O_2$ by microdyalysis following global forebrain ischemia and reperfusion in the rat: Correlation with the cytotoxic potential of $H_2O_2$ in vitro. Brain Res 671 (181-186). $H_2O_2$ causes intracellular glutathione depletion, a molecule that remove $H_2O_2$ from the cell, suggesting that $H_2O_2$ enters the cells and therefore may set in motion one or more toxic pathways in cells. Dringen, Pawlowski and Hirrlinger, 2005. Peroxide Detoxification by Brain Cells. J Neurosci Res 79(157-165); Halliwell and Whiteman, 2004. Measuring reactive species and oxidative damage in vivo and in cell culture: how should you do it and what do the results mean? British Journal of Pharmacology 142 (231-255); Baud, Greene, Li, Wang, Volpe and Rosenberg, 2004. Glutathione Peroxidase-Catalase Cooperativity Is Required for Resistance to Hydrogen Peroxide by Mature Rat Oligodendrocytes. J Neurosci 24(1531-1540).

Cells also synthetize antioxidative molecules and have mechanisms for recycling them. Gluthation (GSH) is one of the principal proteins involved in the antioxidant machinery eliminating $H_2O_2$, together with its oxidized form GSSG and related enzymes glutathione peroxidase (GPx), glutathione reductase (GR), glutaredoxin and NADPH/NADP+. A variety of studies using cell culture models support the crucial role played by GSH in mitochondria as a protective effect in apoptotic cell death. In apoptosis, programmed cell death, oxidation of mitochondrial GSH/GSSG stimulates GSH depletion resulting in increased ROS, suggesting a role for GSH in controlling mitochondrial ROS generation. Dringen, Pawlowski and Hirrlinger, 2005. Peroxide Detoxification by Brain Cells. J Neurosci Res 79(157-165); Dringen, Gutterer and Hirrlinger, 2000. Glutathione metabolism in brain. Metabolic interaction between astrocytes and neurons in the defense against reactive oxygen species. Eur J Biochem 267 (4912-4916).

Another enzyme in the antioxidant machinery that eliminates hydrogen peroxide is catalase. Catalase is a cytoplasmic enzyme that is of special relevance when the clearance of $H_2O_2$ in high concentrations is required. Baud, Greene, Li, Wang, Volpe y Rosenberg, 2004. Glutathione Peroxidase-Catalase Cooperativity Is Required for Resistance to Hydrogen Peroxide by Mature Rat Oligodendrocytes. J Neurosci 24(1531-1540).

It has also been probed that hMSCs possess the main enzymatic and non-enzymatic mechanisms to detoxify reactive species and to correct oxidative damage of proteome and genome that ensure the efficient manage of ROS. Valle-Prieto and Conget, 2010. Human Mesenchymal Stem Cells efficiently manage oxidative stress. Stem Cell Dev 19 (1885-1893). If this potential is maintained in vivo, hMSCs could also contribute to tissue regeneration limiting ROS-induced tissue damage.

Some successful attempts to modify the synthesis of enzymes involved in elimination of ROS describe that human Bone Marrow Stromal Cells cultured in the presence of ascorbate express higher levels of superoxide dismutase, catalase and glutathione (Stolzing and Scutt, 2006. Effect of reduced culture temperature on antioxidant defenses of mesenchymal stem cells. Free Radic Biol Med 41(326-338). Moreover, in the article, Ebert, Ulmer, Zeck, Meissner-Weigl, Schneider, Stopper, Schupp, Kassem and Jacob, 2006. Selenium supplementation restores the antioxidative capacity and prevents cell damage in bone marrow stromal cells in vitro. Stem Cells 24(1226-1235), the authors describe the up-regulation of the basal antioxidant capacity of BMMSCs by modifiying the cell culture conditions with selenium supplementation or temperature reduction. Stolzing and Scutt (2006) published that the temperature reduction in these BMMSC doesn't affect their viability but that increases their differentiation. On the other hand, stem cells directly obtained through the treatment method of the present invention, cells named HC016, don't show any evidence of differentiation, maintaining their undifferentiated phenotype, and also their viability.

Furthermore, Ebert et al., 2006 demonstrate that the selenium supplemetantion of the culture medium of BMMSC with 100 nM sodium selenite exclusively increases the activity of intracellular selenium-dependent enzymes, as glutathione peroxidase (GPx) y la thioredoxin reductase (TrxRs). On the other hand, HC016 cells keep their viability, proliferative capacity and undifferentiated phenotype, and also activate genes coding for key selenium-independent enzymes for ROS detoxification, like superoxide dismutases (SODs) y catalase (Cat), fundamental to ROS detoxification. Moreover, HC016 cells have increased levels of GSH.

To conclude, HC016 cells directly obtained with the treatment method described in the present invention show a series of advantages with respect to the stem cells used in the state-of-the-art, that renders HC016 cells specially suited to act in oxidative stress conditions. These advantages are mainly 1) generation of a superior intracelular pool of the detoxifying molecule GSH, 2) a superior and increased expression of genes coding for enzymes involved in reactive oxygen species elimination, 3) a new cytoskeletal conformation and therefore, an consequently, a higher migration capacity towards damaged areas, and 4) a higher expression of growth factors related to tissue regeneration processes.

These effects acquired by HC016 cells, increase their intracelular and extracelular defenses against ROS, without generating any modification regarding their viability and differentiation state.

WO 2010/150094 describes a method for mesenchymal stem cells in vitro differentiation into adipocytes and its use as a cell therapy. The method described consists in culturing those cells in hypoxic conditions.

WO2007/030870 provides a method for stem cell differentiation, more precisely, cells from human embryos (hES cells), into cardiomyocites and neural progenitors by culturing hES cells in a medium without serum, that additionally contains prostaglandin or a p38MAP Kinase inhibiting molecule.

As a consequence, there is an important need in the state-of-the-art to generate methods for obtaining mesenchymal stem cells with improved or increased own enzymatic and non-enzymatic mechanisms focused on the elimination of reactive oxygen species, and as a consequence, generate cells that could be more effectively used in cell therapies for oxidative stress associated diseases.

OBJECT OF THE INVENTION

The present invention refers to a method of treatment for mesenchymal stem cells, and also the use of these previously treated cells in the care of diseases caused by or related to oxidative stress.

The stem cells of the present invention, can be obtained from different sources, among others, adipose tissue, bone marrow, umbilical cord and/or placenta, but preferably, the present invention is generated from human adipose tissue-derived mesenchymal stem cells, ASC.

In one aspect of the present invention, diseases considered to be associated to and caused by oxidative stress, or conditions of degenerative stress due to components mediated by reactive oxygen species are those selected from the group that consists of: periarthritis, diabetes mellitus, chronic granulomatous diseases, arteriosclerosis, pulmonary fibrosis (chronic obstructive pulmonary disease, COPD, idiopathic pulmonary fibrosis), ischemia/reperfusion syndrome, Alzheimer's disease, Parkinson's disease, rheumatoid arthritis, systemic lupus erythematosus, intestinal inflammatory disease: ulcerative colitis and Crohn's disease, adult respiratory distress syndrome, stroke, spinal cord injury, peripheral nerve injury, amyothrophic lateral syndrome, Huntington's disease, multiple sclerosis, Friedreich's ataxia, periodontitis, diseases of the mucosa, diseases and injuries that co-exist with an inflammatory component, acute and chronic ulcers and wounds.

The oxidative environment present in these pathologies, induces the maintenance and even the intensification of the inflammatory process in the damaged area. This phenomenon is one of the factors that impairs tissue regeneration, which is not able to recover due to the high amount of ROS that is produced. Mesenchymal stem cells treated with the method of the present invention acquire a higher capacity of survival in the oxidative environment produced in the above listed pathologies. This fact produce an increase in soluble factors availability from live cells that promote the recovery of the damaged tissue.

Therefore, one aspect of the present invention is a treatment method for mesenchymal stem cells that includes obtention and isolation of mesenchymal stem cells from a human donor and the culture of these cells in a defined treatment medium.

A preferential aspect of the present invention is the application of the previous treatment method for mesenchymal stem cells obtained from adipose tissue.

It is also an aspect of the present invention a method for the functional modification of mesenchymal stem cells, to promote their survival and increase their capacity of produce molecules involved in the detoxification of reactive oxygen species.

Another aspect of the present invention relates to mesenchymal stem cells obtained with the treatment method of the present invention that have a superior and increased expression of genes involved in the detoxification of reactive oxygen species, and/or superior intracellular levels of GSH and/or citoeskeletal conformational changes and/or an increase in their cellular migration capacity, compared with mesenchymal stem cells non-treated with the preconditioning method of the invention.

Another aspect of the present invention relates to the use of mesenchymal stem cells treated according to the present invention that have superior intracellular levels of GSH, more preferably, a superior and increased expression of genes involved in the elimination of reactive oxygen species, selected from a group that consists in: SOD1 cytoplasmic superoxide dismutase, SOD2 mitochondrial superoxide dimutase 2, SOD3 extracellular superoxide dismutase 3, Cat calatase, GPx glutathion peroxidase y GR glutathion reductase, more preferably, a different citoeskeletal conformation and a superior expression of the gene coding for beta-actin, and also the growth factor IGF-1, as therapeutic formulations/reagents in a cell therapy for the care of diseases caused by or related to oxidative stress.

The present invention also relates to the use of the mesenchymal cells of the present invention administrated in an area adjacent to the damaged tissue, and/or in the epicenter of the lesion.

DESCRIPTION OF THE DRAWINGS

FIG. 6. Fluorescence microscopy images of the F-actin immunostaining. It can be observed an increase in the presence of F-actin in HC016 cells, with respect to ASC, and its distribution in stress fibers, what means cytoskeletal conformational changes in HC016 related with their superior migration and chemotactic capacity (Example 8).

DETAILED DESCRIPTION OF THE INVENTION

The present invention refers in one aspect to a method of treatment for mesenchymal stem cells, preferably from adipose tissue, meaning obtained and/or isolated from adult adipose tissue, and more precisely from animal origin, preferably from human. This procedure requires mostly two defined steps, first, obtaining and isolation of mesenchymal stem cells, and second, a period of growth and specific treatment of cells in a defined treatment medium that includes an oxidative agent.

Acquisition of ASC Cells:

Regarding this step, the procedure includes firstly the acquisition and isolation of the mesenchymal stem cells.

The origin of mesenchymal stem cells can be selected from a group that consist of adipose tissue, bone marrow, umbilical cord and/or placenta, preferably, the present invention is generated from human adipose tissue-derived mesenchymal stem cells, ASC.

Therefore, preferentially, in the present invention, the fraction of adipose tissue-derived mesenchymal stem cells is extracted from lipoaspirates from healthy human patients under anesthesia. The lipoaspirate is donated by patients after the corresponding informed consent. Lipoaspirates are then washed with 1×PBS and digested with collagenase type I for 30 minutes at 37° C. and then centrifuged to obtain a cell pellet. This pellet is resuspended in eritrocyte buffer lysis and the purified cell suspension is filtered through a 100 µm nylon mesh and centrifuged again. After resuspending the cells, these are seeded in culture flasks, to proceed with the cell colony expansion.

Cell colony expansion or subculture processes are used in the present invention include dettachment of cells from the culture containers, by incubation with a trypsin/EDTA solution, centrifuge harvested cell suspension, determine cell density and viability and seed those cells in new cell culture containers.

Cell harvesting in the present invention follows the methodology described in the state-of-the-art, as indicated in the publications: Yoshimura, Shigeura, Matsumoto, Sato, Takaki, Aiba-Kojima, Sato, Inoue, Nagase, Koshima y Gonda, 2006. Characterization of Freshly Isolated and Cultured Cells Derived From the Fatty and Fluid Portions of Liposuction Aspirates. J Cell Physiol 208(64-76); Almeida, Campa, Alonso-Vale, Lima, Daud y Stocchero, 2008. Fracción vascular estromal de tejido adiposo. Cir.plást. iberolatinoam. 34 (71-79); Wagner, Wein, Seckinger, Frankhauser, Wirkner, Krause, Blake, Schwager, Eckstein, Ansorge y Ho, 2005. Comparative characteristics of mesenchymal stem cells from human bone marrow, adipose tissue, and umbilical cord blood. Experimental Hematology 33 (1402-1416).

Cells treatment method. Acquisition of HC016 cells:

Once obtained the appropriate cell number, between 300.000-2.000.000, these are processed with a treatment that requires cells in contact with a defined concentration of an oxidant agent following specific treatment periods.

Oxidative agents are considered, for example, oxides and/or peroxides, among others, hydrogen peroxide ($H_2O_2$), calcium peroxide ($CaO_2$), magnesium peroxide ($MgO_2$), zinc peroxide ($ZnO_2$), manganese peroxide ($MnO_2$), lead peroxide ($PbO_2$), nitric oxide (NO), nitrous oxide ($N_2O$), ozone ($O_3$), sodium perborate ($NaBO_3$), selenium dioxide ($SeO_2$), silver oxide ($Ag_2O$), ferric salts as ferric chloride ($FeCl_3$), cupper salts as cupric hydroxide (CuOH, $Cu(OH)_2$), percanbonates as sodium percarbonate ($2Na_2CO_3$), permanganates as potassium permanganate ($K_2Mn_2O_8$), dichromates as potassium dichromate ($K_2Cr_2O_7$), lithium salts, sodium and calcium of hypochlorous acid (HClO—), sodium chlorite ($NaClO_2$), chloric acid ($HClO_3$), potassium chlorate ($KClO_3$), aluminum hydroxide ($Al_2O_3$), aluminum hydroxide co-precipitated with magnesium carbonate ($MgCO_3$), arsenic trioxide ($As(OH)_3$), benzoil peroxide (($C_6H_5CO)_2O_2$), calcium hydroxide ($Ca(OH)_2$), chlordiazepoxide hydrochloride, cupric acid (CuO), iron oxides, magnesium oxide (MgO), magnesium dioxide, magnesium hydroxide ($Mg(OH)_2$), potassium hydroxide (KOH), sodium hydroxide (NaOH), titanium oxide ($TiO_2$), zinc oxide (ZnO) and other oxidant agents, preferably hydrogen peroxide ($H_2O_2$) that belongs to the group of reactive oxygen species (ROS) which is a waste product of the mitocondrial respiratory chain and a signalling molecule in inflammatory processes. An increase of $H_2O_2$ above certain tolerance values induces cell death. Nonetheless, the present treatment method includes the culture of cells with $H_2O_2$ in controlled manner; this means with controlled periods and methodology and with defined concentrations that trigger new functionalities and characteristics in the mesenchymal stem cells directly obtained with this treatment.

More precisely, the treatment method developed in the present invention includes culturing cells in a moderate oxidative environment, following defined treatment periods.

In general terms, the treatment method includes two consecutive cycles of treatment within a time interval of 48-72 hours, followed by a third treatment cycle of 24-48 hours in experimental container.

In detail, the treatment period includes the following steps:
a) First cycle: Seed cells on a culture container and wait for cell adaptation period between 4 to 8 hours to allow cells to adhere and acquire their typical morphology.
b) Add the treatment medium, composed by DMEM plus 10% FBS and a solution of $H_2O_2$, up to reach a final concentration in the range of 0.01 and 0.05 mM.
c) Keep 48-72 hours in the incubator at 37° C. and a 5% $CO_2$ atmosphere.
d) Second cycle: Renew the treatment medium by replacing it with DMEM plus 10% FBS and a solution of $H_2O_2$, up to reach a final concentration in the range of 0.01 and 0.05 mM.
e) Incubate these cells for 48-72 hours at 37° C. and a 5% $CO_2$ atmosphere.
f) Third cycle: Renew the treatment medium by replacing it with DMEM plus 10% FBS and a solution of $H_2O_2$, up to reach a final concentration in the range of 0.01 and 0.05 mM.
g) Incubate these cells for 48-72 hours at 37° C. and a 5% $CO_2$ atmosphere.

After this treatment period, cells have modified their functional and morphological characteristics. From this point forward, HC016 acronym is now implemented for these cells.

Culture or growth media include the usual known components in the state-of-the-art, these are, therefore, media with high glucose concentration (DMEM, Invitrogen) at a 85-95% of the total volume, with fetal bovine serum at concentrations 5-15% of the total volume (Biochrom) and an antibiotic solution PSA at concentration 1% of the total volume (Invitrogen).

Also, the treatment medium used in the method of the invention described previously includes a high glucose concentration (DMEM, Invitrogen) at a 85-95% of the total volume, with fetal bovine serum at concentrations 5-15% of the total volume (Biochrom), an antibiotic solution PSA at concentration 1% of the total volume (Invitrogen) and hydrogen peroxide ($H_2O_2$) at concentrations between 0.01 to 0.05 mM of the total volume (Panreac).

Characterization of HC016 Cells Compared to ASC Non-Treated with the Method of the Invention As a consequence of the treatment method of the invention, HC016 cells of the present invention have acquired and show a superior and enhanced levels of expression of defined genes involved in elimination of reactive oxygen species, such as the genes coding for the following proteins: SOD1 Superoxide dismutase 1 cytoplasmic, SOD2 superoxide dismutase 2 mitochondrial, SOD3 superoxide dismutase 3 extracellular, GPx glutathion peroxidase, GR glutathion reductase and Cat catalase, compared with ASC non-treated with the method of the invention.

SOD1: The enzyme superoxide dismutase 1 is a dimeric protein that contains cupper (Cu) and Zinc (Zn) as co-factors. SOD1 is in the cellular cytoplasm and catalyzes the dismutation of superoxide, a product of the respiratory chain and the enzyme xanthine oxidase, in oxygen and hydrogen peroxide through the following reactions.

SOD2: The enzyme superoxide dismutase 2 is a tetrameric protein that contains manganese (Mn) as co-factor. SOD2 is localized in cell mitochondria and catalyzes the dismutation of superoxide, a product of the respiratory chain and the enzyme xanthine oxidase, in oxygen and hydrogen peroxide through the following reactions.

$$Mn^{(n+1)+}\text{-SOD} + O_2^- \rightarrow Mn^{n+}\text{-SOD} + O_2$$

$$Mn^{n+}\text{-SOD} + O_2^- + 2H^+ \rightarrow Mn^{(n+1)+}\text{-SOD} + H_2O_2$$

SOD3: The enzyme superoxide dismutase 3 is a homotetrameric protein that contains cupper (Cu) and Zinc (Zn) as co-factors. SOD3 is released to the extracellular medium where it binds the extracellular matrix through heparan sulfate proteoglycan and collagen type I to catalyze the dismutation of superoxide present in the medium, generating oxygen and hydrogen peroxide through the following reaction.

$$Cu\text{—}Zn^{(n+1)+}\text{-SOD} + O_2^- \rightarrow Cu\text{—}Zn^{n+}\text{-SOD} + O_2$$

$$Cu\text{—}Zn^{n+}\text{-SOD} + O_2^- + 2H^+ \rightarrow Cu\text{—}Zn^{(n+1)+}\text{-SOD} + H_2O_2$$

Cat: The enzyme catalase is a tetrameric protein with four peptidic chains and four porphyrin heme groups (Iron, Fe) that is present in the peroxisomes of mostly all of the aerobic cells as a key enzyme in the oxidative stress defense. Catalase reacts with hydrogen peroxide and converts it into water. Althogh its mechanisms are not completely understood, its activity has been described according to the following reactions.

$$H_2O_2 + Fe(III)\text{-E} \rightarrow H_2O + O = Fe(IV)\text{-E}(.+)$$

$$H_2O_2 + O = Fe(IV)\text{-E}(.+) \rightarrow H_2O + Fe(III)\text{-E} + O_2$$

Chelikani, Fita y Loewen, 2004. Diversity of structures and properties among catalases. Cell Mol Life Sci 61(192-208).

GPx: The enzyme glutathion peroxidase is one of the little proteins known in superior vertebrates that contain selenocysteine. GPx is mainly found in the cytoplasm and takes part in the detoxification of hydrogen peroxide generated by superoxide dismutase and monoamino oxidase by catalyzing $H_2O_2$ binding to molecules of reduced glutathion (GSH).

GR: The enzyme glutathion reductase is a homodimeric flavoprotein. GR belongs to the family pyridine nucleotide-disulphite oxidoreductase class I. This enzyme takes part in a fundamental cycle of the antioxidant defense. Its activity consists in reducing the oxidized glutathion (GSSG) to its sulfhydryl form (GSH), which is a key molecule in the antioxidant defense.

The increase in expression of genes involved in detoxification of ROS has been quantified with respect to the non-treated ASC cells, confirming that HC016 cells present an increase in the expression of SOD1 gene of, at least, a 30%, preferably 53%, an increase in the expression of SOD2 gene of, at least, a 25%, preferably 37%, an increase in the expression of SOD3 gene of, at least, a 50%, preferably 77% and/or an increase in the expression of Cat gene of, at least, a 50%, preferably 78%.

The methodology used to quantify the superior expression of genes of HC016 with respect to ASC, has been the following: Cellular lysis, mRNA extraction and purification of each experimental group following the protocol included and described in the SuperScript-III® First Strand membrane filters commercial kit. A volume of mRNA serves as a template for generating cDNA with the Retro Transcription-Polymerase Chain Reaction (RT-PCR) following the reagents and protocols included in the Pure Link™ RNA Micro Kit. Corresponding volumes of cDNA of each experimental group are processed with Polymerase Chain Reaction (PCR) including specific primers that localize DNA fragments present in the genes that code for Superoxide Dismutase 1, 2 y 3 (SOD1-3), Catalase (Cat), Glutathion Peroxidase (GPx) y Glutathion Reductase (GR). PCR products of each experimental group are migrated by electrophoresis and the size of the amplified fragment is determined and the intensity of each band is quantified. The resulting value is normalized with the value of the intensity of a defined constitutive gen, Gliceraldehyde-3-Phosphate Deshydrogenase, GAPDH Moreover, it has been demonstrated that HC016 cells have a superior level of intracelular GSH of at least 8%, preferably 10%, with respect to ASC cells. The method used to quantify the superior level of GSH in HC016 cells with respect to ASC has been the Tietze's enzymatic method, as described below: The experimental groups are two independent batches of cells, ASC and HC016. After the treatment, cells are harvested, their proteins extracted by incubating cells in lysis buffer and the total protein in the supernatant is quantified following the protocol and reagents supplied with the BioRad DC Protein assay kit. In a different aliquot of the supernatant proteins are precipitated and the supernatant is transferred for total GSH and GSSG quantification. Samples for the total GSH and GSSG assays are processed in triplicates in a 96 well-plate. For GSH measurement, samples are incubated with glutathion reductase and after this absorbance at 405 nm is measured each 15 seconds during 2.5 minutes. For GSSG measurement, purified sample proteins are pre-treated with 2-vinilpiridina, later on with glutathion reductase and finally absorbance at 405 nm is measured each 15 seconds during 30 minutes.

Absorbance values are extrapolated to a standard curve generated by repetition of these previously described steps but instead of using cell protein samples, using known GSH concentrations. Values are expressed as nmol/mg of protein. Total glutathion is calculated as: $GSH_{total} = GSH_{reduced} + 2GSSG_{oxidazed}$ Additionally, HC016 cells are characterized by presenting inferior levels of intracellular ROS in at least 10%, preferably 11%, more preferably 15% compared with ASC.

The method selected to quantify the superiority in HC016 intracellular ROS levels with respect to ASC has been a DCFA probe-based fluorimetric quantification: The experimental groups consist of four independent populations, one of ASCs, a second of HC016, a third of intact HOG cells, and a fourth one of HOG cultured with the same treatment that generates HC016 from ASC. Cells are washed with PBS1× and then 2',7'-dichlorodihydrofluorescein diacetate (DCFA) 10 µM added for 30 minutes. Later on, DCFA is washed out and new medium is added. Then, cells are cultured with an oxidant medium by adding $H_2O_2$ to the medium in a concentration gradient of 0, 0.1, 0.25, 0.5 and 1 mM and right after this, intracellular ROS levels evolution is measured each 5 minutes and for a total of 60 minutes in a fluorimeter plate reader. Graphs are represented as arbitrary fluorescence units of intensity along time (minutes).

Figure 5:
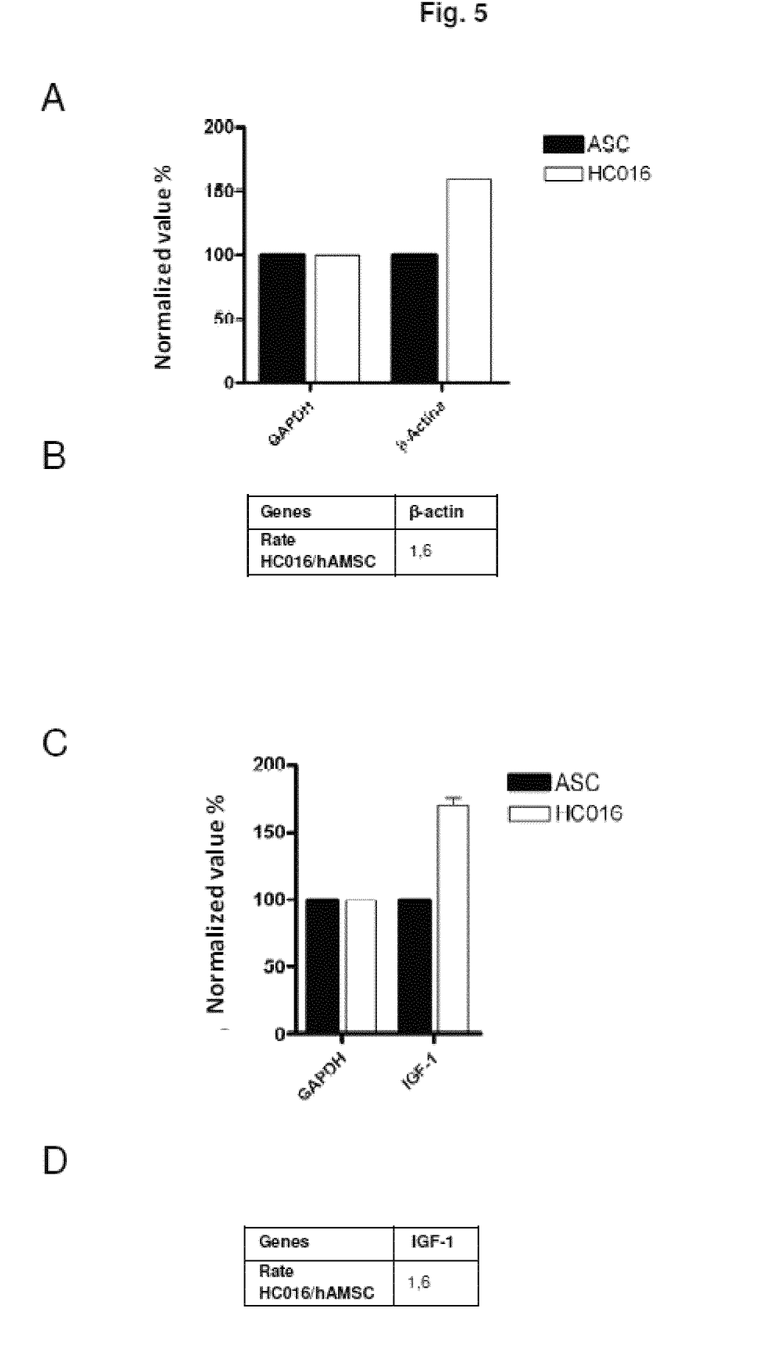
FIG. 5A. Expression levels of genes involved in cytoeskeletal composition (β-Actin) in ASC and HC016 cells (Example 7).
FIG. 5B. Quantification of the expression of genes involved in cytoeskeletal composition (β-Actin) in ASC and HC016 cells (Example 7). Value is expressed as ratio HC016/ASC (Example 7).
FIG. 5C. Expression levels of the gen coding for the growth factor IGF-I in ASC and HC016 cells (Example 7).
FIG. 5D. Quantification of the expression of the gen coding for the growth factor IGF-I in ASC and HC016 cells (Example 7). Value is expressed as ratio HC016/ASC (Example 7).
Figure 6:
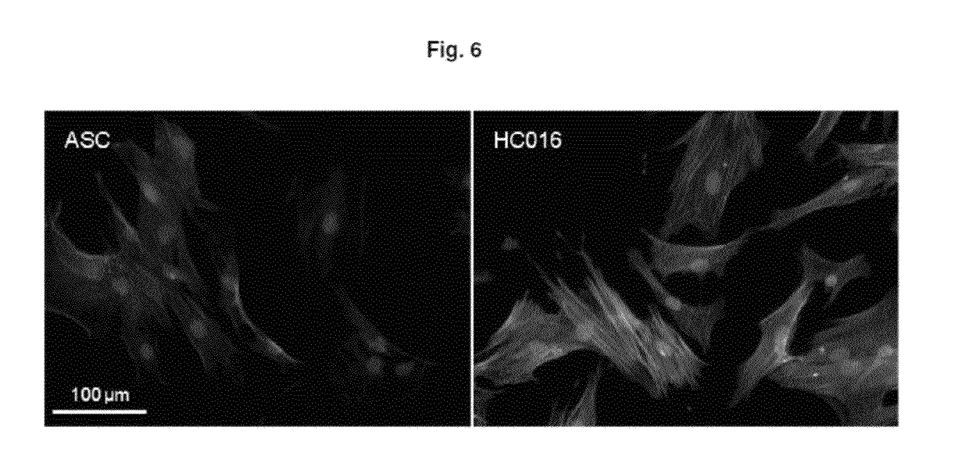
Figure 8:
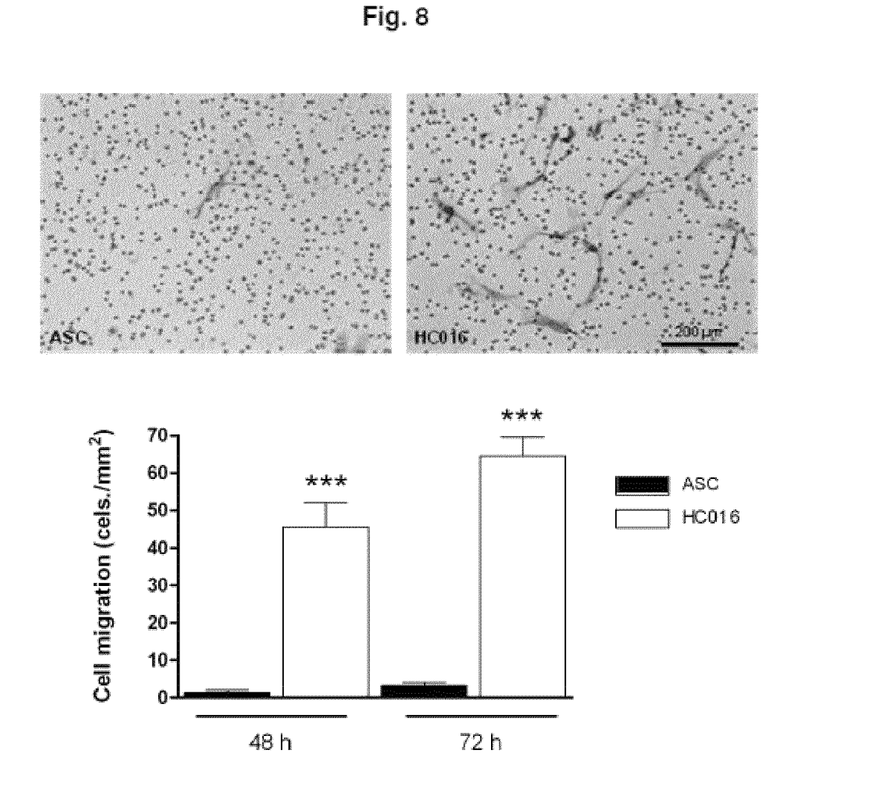
FIG. 8. Representative images and quantitative bar graph showing the significative superior migration capacity of HC016 cells, with respect to ASC cells, towards cells suffering an oxidative stress insult (Example 10).

Additionally, HC016 cells treated according to the method of the present invention, show a superior migration capacity. This property determines that HC016 can access more efficiently to the damaged tissue area and initiate their trophic action to protect damaged cells and influence the control of an adverse environment. This significative higher migration capacity with respect to ASC, is determined by conformational changes that occur in the cytoskeleton of HC016, and also an increase in the type of microfilaments (beta-actin) organized at the cell expansion border. These cell membrane projections are the physical substrate for cell motion during migration. At this point, beta-actin gene expression analysis shows an increase in HC016 of 59% with respect to ASC (FIG. 5 A-B). Moreover, polymerized actin or F-actin immunostaining indicates relevant morphological changes related to a higher motility capacity, as the formation of stress fibers, a fundamental element in migration events. FIG. 6 shows immunostaining of F-actin arranged in stress fibers, which is one of the critical aspects in cell migration process (Mitchison et al., 1996). Also, the experiment exclusively performed to analyze cell migration capacity by means of Boyden chambers (FIG. 8, example 10), shows that HC016 cells have a 30-fold higher migration capacity with respect to ASC.

Additionally, HC016 cells, present an increase in insulin-like growth factor-1 (IGF-1) gene expression of 64% with respect to ASC (FIG. 5 C-D). Previous studies have shown that IGF-1 intermediates relevantly in regenerative processes occurred after a damage. IGF-1 is a potent neurotrophic factor produced by non-neuronal cells after a damage to nerve tissue, stimulating tissue regeneration. IGF-1 promotes neuronal survival, neurite growth, nerve cell proliferation, mielinization and improves axon-Schwann cell interaction (Apel et al., 2010). Moreover, in other experimental models, it has been probed that local application of IGF-1, allows damaged skeletal muscle repair without scar tissue formation and a higher recruitment of stem cells to the damaged area (Spangenburg et al., 2010). Because of these reasons, IGF-1 expression induction in HC016 cells can promote ASC regenerative capacity, in such a way that it increases, cell proliferation capacity, functional recovery of damaged tissue cells and the recruitment of stem cells to the damaged area to contribute to the recovery process.

The method selected for analyzing gene expression with respect to ASC has been the following: This comparative analysis requires two experimental groups that consist of ASC and HC016 cells. Once the treatment method has been completed, each cell group is harvested, lysed, and RNA is extracted and purified, and is processed to obtain cDNA. PCR reaction is performed including specific primers that localize DNA fragments present in the genes that code for β-actin and insulin-like growth factor-1 (IGF-1). PCR products of each experimental group are migrated by electrophoresis and the size of the amplified fragment is determined and the intensity of each band is quantified. The resulting value is normalized with the value of the intensity of a defined constitutive gen, GAPDH This set of data indicate that the treatment method that generates HC016 induces the synthesis of a "pool" of intra- and extra-cellular molecular machinery required for the elimination of $H_2O_2$ and the control of an adverse oxidative environment. HC016 cells have a higher migration capacity to reach the damaged tissue area and also, produce a higher amount of thophic factors that exert their effect on the regenerative processes of cells of damaged tissue and sustain their survival.

Use of HC016 cells in treatment of diseases assotiated with or resulting from oxidative stress.

As discussed above, the characteristics of HC016 cells indicated in the previous section make them especially suitable for the treatment of diseases caused by oxidative stress or degenerative conditions of evolution due to components mediated by reactive oxygen species.

One of the pathologies affecting the central nervous system and is involved the oxidative stress, resulting in degenerative changes due to components mediated by reactive oxygen species, is the spinal cord injury.

Spinal cord injury constitutes a damage in nerve tissue in which pathogens are not involved, and is not induced by external nor genetic factors. At the point of injury, the immediate consequences of trauma are tissue compression, hemorrhage, edema, oxygen depletion and nutrients in the impact zone (Lu, Liang, Chen, Chen, Hsu, Liliang, Lin y Cho, 2004. Injury severity and cell death mechanisms: Effects of concomitant hypovolemic hypotension on spinal cord ischemia-reperfusion in rats. Exp Neurol 185: 120-132; Fehlings y Tator, 1995). The relationships among the severity of spinal cord injury, residual neurological function, axon counts and counts of retrogradely labeled neurons after experimental spinal cord injury. Exp Neurol 132: 220-228). These biological phenomena induce two cellular defense mechanisms: programmed cell death or apoptosis (Yukawa, Lou, Fukui y Lenke, 2002. Optimal treatment timing to attenuate neuronal apoptosis via Bcl-2 gene transfer in vitro and in vivo. J Neurotrauma 19: 1091-1103) and the innate immune reaction (Carpentier y Palmer, 2009. Immune influence on adult neural stem cell regulation and function. Neuron 64: 79-92) that extend to undamaged surrounding areas and persist for weeks or even months after the injury in terms of tissue ischemia and inflammation, in other words, producing a secondary damage (Lu, Liang, Chen, Chen, Hsu, Liliang, Lin y Cho, 2004. Injury severity and cell death mechanisms: Effects of concomitant hypovolemic hypotension on spinal cord ischemia-reperfusion in rats. Exp Neurol 185: 120-132).

These two types of tissue response are expanded along the spinal cord and affect to initially healthy tissue, since the mechanisms available for nerve tissue to respond against its physiological consequences are insufficient.

The expansion is carried out largely through reactive oxygen metabolites (MROs) characteristic of the innate immune reaction that cause oxidative stress and depending on its intensity, can induce apoptosis (Liu, Liu, y Wen, 1999. Elevation of hydrogen peroxide after spinal cord injury detected by using the Fenton reaction. Free Rad Biol & Medicine 27: 478-482; Yukawa et al., 2002). Of these, the most abundant MRO is hydrogen peroxide ($H_2O_2$), that diffuses into the extracellular environment that surrounds nerve cells and spreads in the form of secondary damage. The $H_2O_2$ reacts and degrades membranes, proteins and DNA of cells (Braughler y Hall, 1989. Central Nervous System trauma and stroke. I. Biochemical considerations for oxygen radical formation and lipid peroxidation. Free Radic Biol Med. 6: 289-301) and ultimately induce them to programmed cell death or apoptosis (Yukawa et al., 2002). $H_2O_2$ is also a waste product of normal cells, so they have some defenses against this molecule (Phillis, 1994. A "radical" view of cerebral ischemic injury. Prog Neurobiol 42: 441-448). However, the levels of $H_2O_2$ that are generated after injury are higher than those physiologically tolerable (Hyslop, Zhang, Pearson y Phebus, 1995. Measurement of striatal $H_2O_2$ by microdialysis following global forebrain ischemia and reperfusion in the rat: Correlation with the cytotoxic potential of $H_2O_2$ in vitro. Brain Res 671: 181-186). Among nerve cells, oligodendrocytes, cells that generate the myelin sheat that cover the axon of neurons are more vulnerable to MROs because they have fewer defenses against them, and contain molecules that turn them into targets of secondary damage (Dringen R, Pawlowski P y Hirrlinger J. 2005. Peroxide detoxification by brain cells. J Neurosci Res 79: 157-165). Therefore, in addition to the initial cell death after injury, oxidative damage due to subsequent $H_2O_2$ causes a persistent demyelization of nerve fibers, that reduces the conduction of the nerve signal through them (Nashmi R y Fehlings MG. 2001. Changes in axonal physiology and morphology after chronic compressive injury of the rat thoracic spinal cord. Neuroscience 104: 235-251).

Other diseases are those selected from the group consisting of periarteritis nodosa, diabetes mellitus, chronic granulomatous disease, arteriosclerosis, stroke, pulmonary fibrosis (chronic obstructive pulmonary disease, COPD, idiopathic pulmonary fibrosis), ischemia-reperfusion syndrome, Alzheimer's, Parkinson's, rheumatoid arthritis, lupus erytematosus, inflammatory bowel disease: ulceratice colitis and Chron's disease, respiratory distress syndrome in adults, atherosclerosis, spinal cord injury, peripheral nerve injury, amyotrophic lateral sclerosis, Huntington's disease, Friedeich's ataxia, periodontitis, mucosal diseases and illnesses and injuries that occur with a component inflammation, acute and chronic ulcers and wounds.

The administration of HC016 cells to the affected area decreases the level of oxidative stress caused as a result of the activation of immune cells during inflammatory processes.

Additionally, the administration of HC016 cells to the affected area reduces the levels of oxidative stress arising as a result of the production of MROs after internal bleeding, improves the secretion of paracrine cytokines, interleukins, chemokines, trophic factors and growth factors, increases survival and proliferation of other mammalian cells, decreases the levels of extracellular MROs in the vicinity of mammalian cells close to administered HC016 cells and decreases extracellular levels of signaling molecules such as pro-inflammatory TNF-alpha, IL-1 beta, etc.

Furthermore, the HC016 cells have a significative higher chemotactic capacity toward damaged cells by extracellular $H_2O_2$, as demonstrated in Example 10 of the present invention.

The use of HC016 cells includes the administration of mesenchymal cells previously treated in an area adjacent to the site of damage, rather than the epicenter of the injury, in order to limit the irradiation of tissue damage, the extent of the injury and the functional loss.

The tissue in the injury suffer severe compressive force that breaks the membranes of nerve cells and cells of the vascular system. Also, as a result of the injury, could be bleeding due arteries and veins rupture, a disruption of organelles, cytoplasm, vesicles and cell membrane, facts that will lead to tissue necrosis. These events are inherent to the lesion. Later, if these are not addressed, the molecules released by necrotic cells, along with other molecules released also by immune system cells, expand the damage to injury adjacent areas through cell signaling molecules such as $H_2O_2$. The application of this mesenchymal cell based therapy is designed to reduce or minimize the spread of tissue damage. Therefore, the application of cell therapy will preferably be in an area adjacent to the epicenter of injury.

In another aspect of the invention, the treated cells will be applied using a route of administration, that allow them to directly reach the epicenter of the injury, in order to metabolize reactive oxygen species in the area, reduce oxidative stress and control inflammatory status, to avoid the situation of massive cell death in this area.

The routes of administration may be, any parenteral route (such us intraarterial, intravenous, intralymphatic, intraraquídea, epidural, intramedullary), subcutaneous, intramuscular, intraperitoneal, transdermal (percurtaneous), intraarticular, intratracheal, intraalveolar, intrathecal, intraocular, conjunctival, intracardiac, intranasal, vaginal, urethral, cutaneous, rectal, sublingual, oral, oral transmucosal. To carry out these applications, the cells obtained by the method of the present invention are formulated in the appropriate pharmaceutically acceptable vehicles that are already known to those skilled in the art, depending on the route.

Among others, the formulation provides a solution that in addition to cells HC016 contain among others, Ringer-Lactate, human albumin (CSL-Behring), etc, that dispose for administration in glass vials, sterile and non pyrogenic (Sword Scientific).

Similarly, the HC016 cells can be incorporated into biomaterials of natural origin and/or synthetic, for the generation of cell and tissue engineering therapies such as hydrogels, foams and polymeric materials, composites, calcium phosphate derivatives and metallic materials, that enables a better management of the cells to the injury site and increase survival and functionality of the cells, as appropriate.

After HC016 cells administration to mammals, mesenchymal cells migrate toward the injury site, where they activate the proliferation of cells adjacent to the injection site. Preferably, these cells have the same phenotype adjacent to the parenchyma in which the injection has been applied and are precursor cells. Even more preferably, the cell phenotype matches that of adjacent parenchyma cells and the precursor cells.

In another aspect of the invention, the administered mesenchymal HC016 cells remain in the tissue. In addition, the presence of mesenchymal cells administered in the patient's tissue does not induce an immune response against those administered mesenchymal cells.

EXAMPLES

Example 1

Obtaining of Mesenchymal Cells from Adipose Tissue (ASC)

Mesenchymal stem cells from adipose tissue are isolated from human tissue following the methodology described by Yoshimura et al., 2006, Almeida et al., 2008, Wagner et al., 2005.

The fraction of mesenchymal stem cells from adipose is obtained from lipoaspirates of healthy patients under anesthesia. The lipoaspirate is washed with PBS 1× and digested with collagenase type I for 30 minutes at 37° C. and then centrifuged to obtain a cell pellet. This pellet is resuspended in erythrocyte lysis buffer and purified cell suspension is passed through 100 µm filter and centrifuged again. After resuspending the cells, these are seeded in culture media for cell expansion.

The cells are cultured as primary cultures for a period of 5 days in a growth medium composed by DMEM (Invitrogen) with 10% fetal calf serum (Biochrom) and 1% antibiotic-antimycotic PSA (Invitrogen), in the incubator at 37° C. and 5% $CO_2$.

Consecutively, the cells are expanded when acquire semi-confluence. For this process the cells are detached from the culture surface using a solution of 0.05% trypsin/EDTA, centrifuged and resuspended in fresh medium. The cell density and viability is determined in the obtained cellular suspension and seeded in a new cell culture surface.

Example 2

Application of the Treatment of the Invention to Cells ASC: Obtaining Cells HC016

350,000 of subcultured ASC cells are seeded in a T25 culture flask with 5 ml of growth medium with the following composition: DMEM (Invitrogen) with 10% fetal calf serum (Biochrom) and 1% PSA antibiotic-antimycotic (Invitrogen) and incubated at 37° C. and 5% $CO_2$, until its adherence.

First cycle: add the treatment medium that contains the following composition: DMEM (Invitrogel) with 10% fetal calf serum (Biochrom), 1% antibiotic-antimycotic PSA (Invitrogen) and 0.01% $H_2O_2$ (Panreac). These cells are incubated in this medium for 48 hours.

Second cycle: after 48 hours the cells are obtained and again 350,000 cells are seeded into a second T25 culture flask and incubate for 4 hours at 37° C. and 5% $CO_2$ until their adherence. Consecutively, the treatment medium is added and cells were incubated for 48 hours.

Third cycle: after these 48 hours the cells are obtained and again 350,000 cells are seeded into a second T25 culture flask and incubate for 4 hours at 37° C. and 5% $CO_2$ until their adherence. Consecutively, the treatment medium is added and cells were incubated for 48 hours.

After these 48 hours, ASC treated cells are renamed HC016.

Example 3

Comparative Analysis of Cell Proliferation of HC016 Cells with Respect to ASC

The analysis of cell proliferation is performed in following experimental four groups: ASC, HC016, intact HOGcells and HOG cells cultured with the treatment of the invention that generates the HC016.

HOG cells are human cells from an oligodendroglioma considered as an experimental oligodendroglial model of neural lineage. HOG cells are cultured undifferentiated with proliferative capability and oligodendroglial genetic background.

ASCs are cultured with the methodology and the growth medium defined and described in Example 1 to generate the cell population for this experiment. A batch of the same number of HC016 cells were generated according to Example 2. HOG cell population were generated by the methods for ASC and HC016 according to Example 1 and Example 2, respectively.

Once prepared the four cell populations, cells are seeded in 96 well plates with growth medium until they are attached to the well. Then the cells are grown in oxidative environment by exposure to 0.1 mM $H_2O_2$. The proliferation was measure following the protocols and reagents of Cell Proliferation MTT method at different times: 0, 24, 48 and 72 hours. According to the kit manufacturer, this test produces a colorimetric estimation of cell proliferation, and therefore this parameter is analyzed and compared in the four cell types.

The figures are represented in arbitrary units of fluorescence intensity over time (hours).

Results

Figure 1:
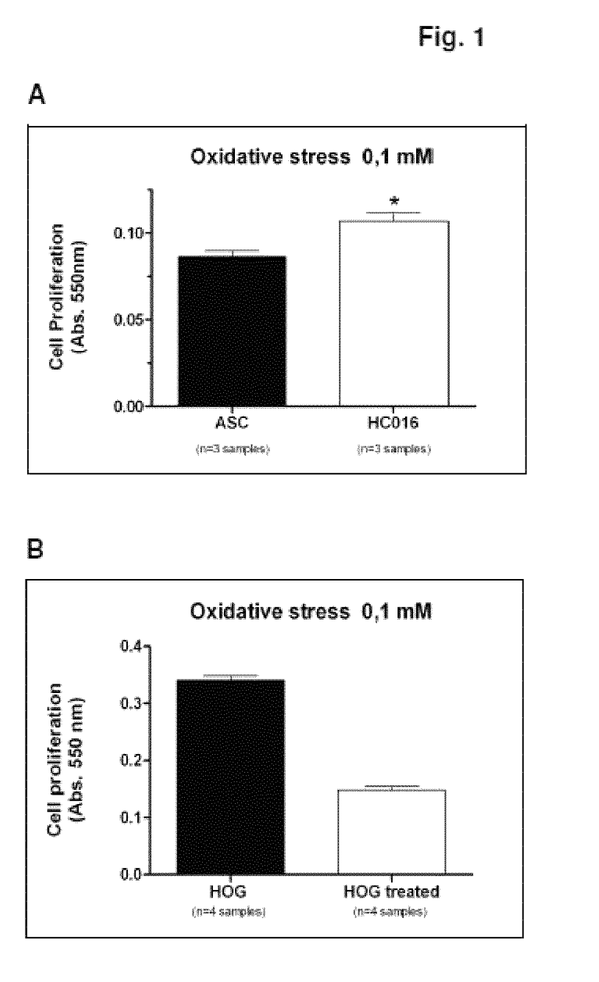
FIG. 1. Proliferative capacity measured by MTT method of ASC, HC016 (A), HOG and HOG treated with the method of the invention (B), and stressed with an oxidative environment (100 µM). It can be observed that HC016 cells have a significative increase in cell proliferation when they are stressed in an oxidative environment. This effect does not occur when the same treatment is applied to other mammal cell type like HOG cells. Asterisk indicates $p<0.05$ in a t-Student test. (Example 3).

The proliferative capacity of HC016 is 1.23 times higher than the control population of ASC at 72 hours after the oxidative stimulus (increase of 23%)(student t-test p<0.05; n=3 samples) (FIG. 1A). This effect is not shared by the other human cells, the HOG oligodendrocytes (FIG. 1B). The treatment of the present invention is effective in ASC but could not be effective in other cell types such as HOG oligodendrocytes.

Example 4

Levels of Intracellular Reactive Oxygen Species in HC016 Cells

The analysis of intracellular levels of reactive oxygen species is performed in four experimental cell groups: ASC, HC016, intact HOGcells and HOG cells cultured with the treatment of the invention that generates the HC016.

Once prepared the four cell populations, cells are seeded in well plates with growth medium until they are attached to the well. Then the cells were briefly washed with 1×PBS, then the PBS is replaced by 100 µl of 1×PBS with the probe 2',7'-dichlorodihydrofluorescein diacetate (DCFA) 10 µM an the cells incubated for 30 minutes. DCFA was subsequently removed and fresh medium is added. Then, the cells were cultured in a medium with $H_2O_2$ at different concentrations: 0, 0.1, 0.25, 0.5 and 1 mM. A time course of MROs levels is measures each 5 minutos for a total of 60 minutes on a fluorimeter plate reader. The ranges of wavelengths of excitation/emission are 485/538 nm.

The figures are represented in arbitrary units of fluorescence intensity over time (minutes).

Figure 2:
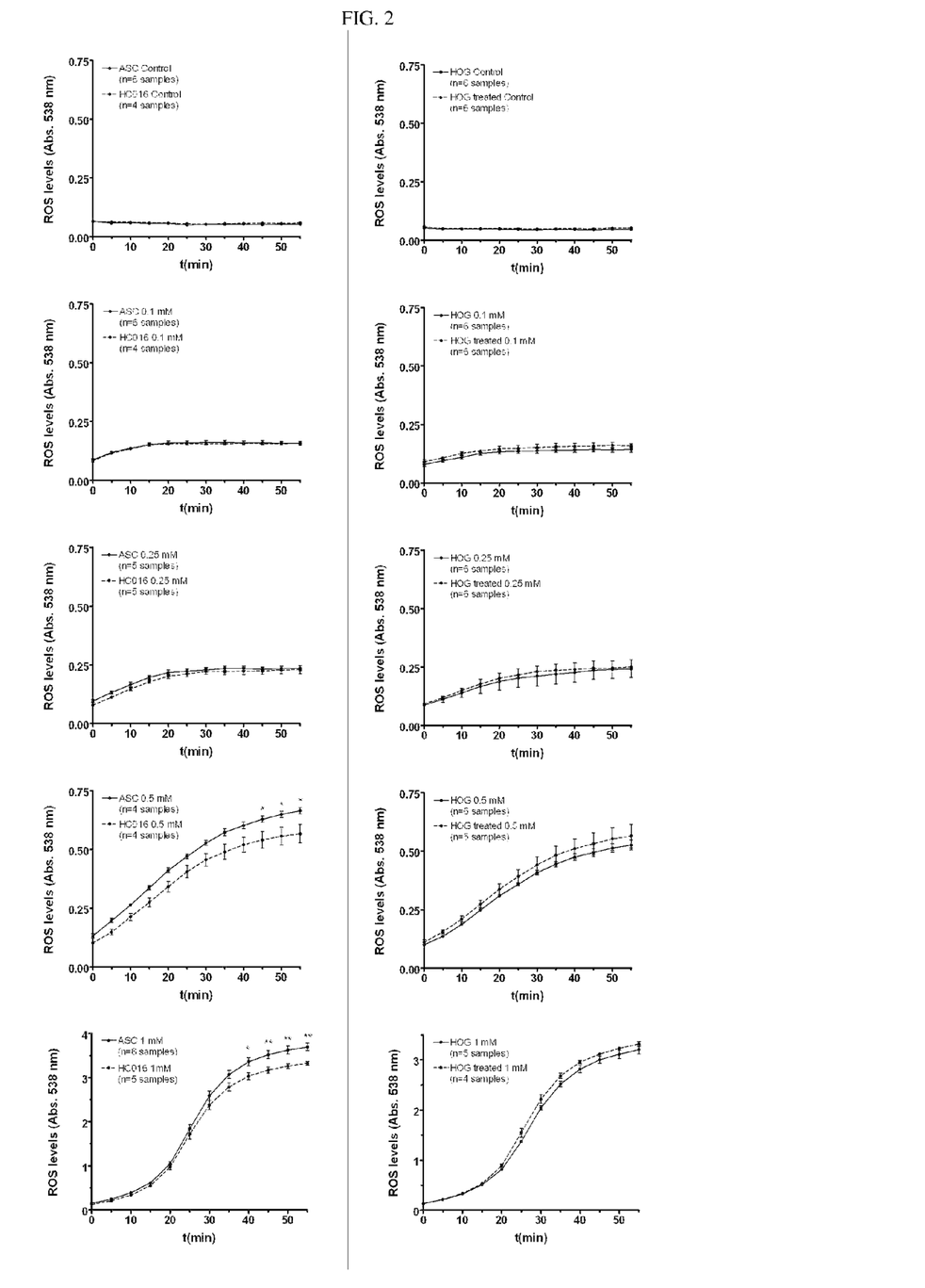
FIG. 2. Kinetic analysis of intracellular levels of reactive oxygen species in ASC, HC016, HOG and HOG treated with the method of the invention. This analysis shows that only HC016 cells significatively decrease intracellular ROS levels, mostly when they are exposed to high concentrations of oxidative stress. Asterisks indicate statistical significative difference according to a two-way ANOVA test (*, $P<0.05$; **, $P<0.01$) (example 4).

Results 55 minutes after being exposed to a gradient of $H_2O_2$, HC016 cells contain significative lower levels of intracellular MROs with 1 mM and 0.5 mM of $H_2O_2$, with respect to ASC (11% lower), two-way ANOVA test P<0.031 and (15% lower), two-way ANOVA test (P<0.039, respectively) (FIG. 2). The treatment that generate HC016 from the ASC does not induce the same response in other mammalian cells like HOG oligodendroglial cells (FIG. 2). In addition, the presence of lower intracellular levels of ROS in HC016 cells, indirectly indicates that the extracellular levels of this molecule also reduces so the HC016 cells have a greater capability to remove the hydrogen peroxide from the environment, making cells with a higher capacity of $H_2O_2$ detoxifying at the site of application such as cell therapy.

Example 5

Levels of Intracellular Total Glutathione (GSH)

The experimental groups consist of two separate batches of ASCs and HC016. The ASC has been cultured with the methodology and the mediums described above. The ASCs have been extracted and isolated from human adipose tissue using the methods described and subcultured in growth medium until the needed cell population was obtained for this experiment. Also a batch of HC016 cells was generated with the same number of cells with the methodology of the invention.

After cell conditioning step, the cells are collected by digestion with 0.05 trypsin/EDTA, the proteins are extracted by incubating the cells with a lysis buffer (protease inhibitor, EDTA and Triton X-100 in buffer sodium phosphate at pH 7.5) and total protein in the supernatant is quantified following the protocol and reagents supplied by BioRad DC protein assay kit.

In another aliquot of the supernatant, proteins are precipitated with 5% sulfosalicilic acid and centrifuged, and low mass peptides dissolved in the supernatant transferred for the total GSH and GSSG assays.

Samples for total GSH and GSSG assays are processed in triplicates in a 96-well plate. For GSH measurement, the samples contain 5% of purified protein sample, 45% of distilled water and 50% of reaction buffer (0.2 M EDTA, DTNB 1.2 mg/100 µl, 3.6 mg NADPH and 4.5 Units of glutathione reductase in sodium phosphate buffer 0.1 M at pH 7.5). Then, absorbance at 405 nm is measured each 15 seconds during 2.5 minutes. For GSSG measurement, purified protein samples are pre-treated with 2-vinylpiridine in a relation 96.3%/3.7% (protein/reagent) and are incubated for 1 hour at 4° C. Then, samples for analysis are prepared containing 10% of the pretreated sample, 40% distilled water and 50% of reaction buffer (0.2 M EDTA, DTNB 1.2 mg/100 µl, 3.6 mg NADPH and 4.5 Units of glutathione reductase in sodium phosphate buffer 0.1 M at pH 7.5). Then, absorbance at 405 nm is measured each 15 seconds during 30 minutes.

Absorbance values are extrapolated to a standard linear fit generated by repeating the same steps with known GSH concentrations. The values are expressed as nmol/mg of protein. Total GSH is calculated as GSH+2GSSG.

Results

Figure 3:
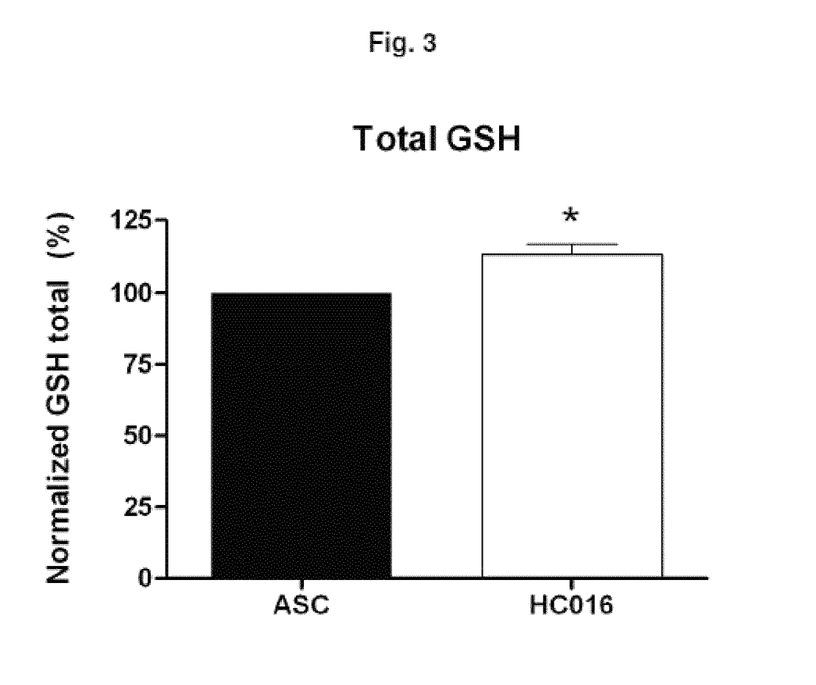
FIG. 3. Intracellular levels of total glutathion ($GSH_{total}$) in ASC and HC016 cells (Example 5). In control conditions, non-stressed, the treatment induces a 10% increase in HC016 basal GSH levels over ASC.

HC016 cells show a higher basal content in total GSH with respect to ASC (FIG. 3) (10% higher). The presence of these higher levels of intracellular total GSH in HC016 cells confirms also the higher detoxification capacity of these cells of toxic agents, conferring a higher resistance to environmental stress or to cellular metabolic activity increase.

Example 6

Levels of Expression of Genes Involved in Metabolite Reactive Species Detoxification This comparative analysis required two experimental groups that consist of ASC and HC016 cells. Conventional ASC are cultured with the methodology and medium described above to obtain the cell population needed for this experimentation. A batch of similar cell number of HC016 are generated applying the method described in example 2.

Once the conditioning procedure is completed, each cell group is harvested from the cell culture container by trypsin/EDTA digestion. Cells are lysed and total mRNA of each experimental group is separately extracted and purified by using a commercially available membrane filters system that retain cell membrane fragments and proteins. Eluted mRNA is converted into cDNA by a Retro Transcript-Polymerase Chain Reaction (RT-PCR) following a established protocol and reagent included in a commercial kit (Pure Link™ RNA Micro Kit; Invitrogen; Ref. 911811). Corresponding volumes of the obtained cDNA of each experimental group are mixed with volumes and concentrations suited to perform a Polymerase Chain Reaction (PCR) including custom-designed primers sequences that bind to specific cDNA fragments localized in exon regions of the gene of Super Oxide Dismutase 1, 2 and 3, Catalase, Glutathion Peroxidase and Glutathion Reductase. PCR products of each experimental group are migrated in an agarose gel by electrophoresis technique (4% agarose in 1×TAE buffer) plus a volume of defined concentration of commercial DNA staining reagent (SYBR Safe DN gel stain; Invitrogen; S33102). Gels are transilluminated with UV light and optical density by a digital image system is acquired to measure the optical density of each migrated band. The value of optical density of each the band of each experimental group and each selected gene is background subtracted and normalized to the value of the optical density of a defined constitutive gene expression.

Results

Figure 4:
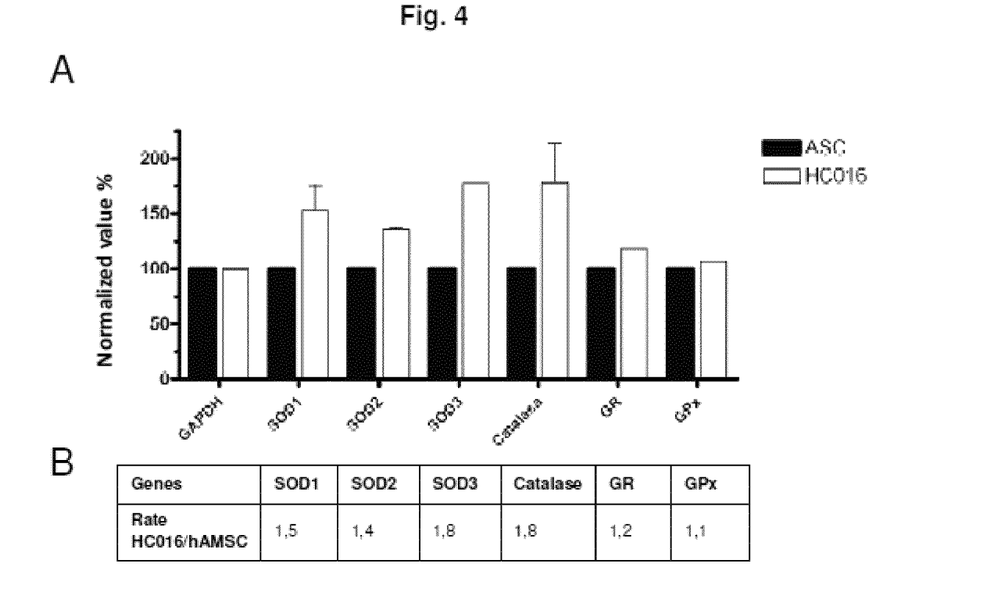
FIG. 4A. Expression levels of genes involved in detoxification of reactive oxygen species in ASC and HC016 cells (Example 6).
FIG. 4B. Quantification of the expression of genes involved in detoxification of reactive oxygen species (SOD1, SOD2, SOD3, Cat, GR, GPx) in ASC and HC016 cells. Values are expressed as ratio HC016/ASC (Example 6).

The expression levels of genes involved in oxidative metabolism of HC016 cells are different from the ASC (FIG. 4A). The quantification of the expression of different genes shows that HC016 cells present a 53% increase of SOD1 gene compared to the ASC, 37% of SOD2 gene, 77% of SOD3, 78% of Cat gene, 18% of GR gene and 6% of GPx gene (FIG. 4B). These results let us conclude that HC016 cells present an improvement in the intra and extracellular antioxidant defenses with respect to ASC (FIG. 4A).

Example 7

Levels of Expression of Genes and Proteins Involved in Cytoeskeleton, and Growth Factors Secretion This comparative analysis required two experimental groups that consist of conventional ASC which are cultured with the methodology and medium described above to obtain the cell population needed for this experimentation, and a batch of similar cell number of HC016 that are generated by the methodology described in example 2. As in example 6, when the conditioning procedure has finished, each cell group is harvested by trypsin/EDTA digestion, cells are lysed, total mRNA is separately extracted and purified and mRNA is converted into cDNA. PCR is performed with the cDNA including custom-designed primers sequences that bind to specific cDNA fragments localized in exon regions of the gene of β-actin and IGF-1. As in Example 6, PCR products of each experimental group are migrated in an agarose gel by electrophoresis technique. Optical density of each migrated band is measured and its value is background subtracted and normalized to the value of the optical density of a defined constitutive gene expression, GADPH.

Results

The expression levels of genes associated with cytoskeletal components and growth factors in HC016 cells when compared with ASC (FIGS. 5A and C). The quantification of the expression of different genes shows that the HC016 cells present a 59% increase of β-actin gene (FIG. 5B) and 64% increase of IGF-I gene compared to ASC (FIG. 5D).

Example 8

Composition and Arrangement of Cytoeskeletal Molecules

This comparative analysis required two experimental groups that consist again of conventional ASC which are cultured with the methodology and medium described above to obtain the cell population needed for this experimentation, and a batch of similar cell number of HC016 that are generated by the methodology described in example 2.

Cells of both populations are seeded on 24-well plates with medium and methodology described above. Once cells are adhered, medium is removed and cells briefly washed with PBS 1×. Then cells are fixed with 4% formaldehyde in PBS 1× for 12 minutes, permeabilized with 0.1% of Triton X-100 in PBS 1× during 10 minutes at 4° C., washed again in PBS1× and incubated with 100 µg/ml of Phalloidin-FITC (Sigma-Aldrich; Ref. P5282) in PBS 1× for 1 hour at room temperature (≈23° C.). Then, cells were extensively washed with PBS 1×, nuclei stained with Hoescht 33258 (Invitrogen; Ref. H1398) and finally covered with a thin layer of Fluoromont-G (Southern Biotech; Ref. 0100-01), and visualized at a fluorescence microscope.

Results

The cytoskeleton of HC016 cells has more F-actin filaments and they are thicker than the ASC cells, and are organized in stress fibers. The observation of ASC and HC016 cells under the microscope show qualitatively that HC016 cells have more F-actin filaments and thicker than ASC (FIG. 6) which gives a more robust cytoskeleton and more prepared for a possible structural remodeling. In Example 7 is shown the quantification of the expression of the gene encoding for F-actin and β-actin monomers, (FIG. 5A-B). Both two results indicate the increased synthesis of F-actin, and this latter result, the effect on the cell cytoskeleton.

Example 9

Protection Capacity of Neural Lineage Cells by HC016 Cells

Experimental groups consist of control oligodendroglial HOG cells without any modification in the normal culture procedure, HOG cells cultured in an oxidant environment, coculture of ASC with HOG cells in an oxidant environment and coculture of HC016 cells with HOG cells in an oxidant environment.

HOG cells are human oligodendroglioma cells considered as an experimental oligodendroglial model of neural lineage. HOG cells are cultured undifferentiated with proliferative capability and oligodendroglial genetic background.

Populations with similar cell numbers of ASC and HC016 cells are generated with the methods described in Example 1 and 2. At the day of the experiment cells are harvested by 0.05 trypsin/EDTA digestion prior to be included in the in vitro co-culture system based on Boyden chambers inserted in 24-well plates (inserts of transwell chambers) that avoid physical contact between two cell populations.

At the day of the experiment, oligodendrocytes are plated and adhered to the bottom of 24-well plates and cultured in an oxidant environment for 1 hour by adding 0.5 ml of 0.5 mM of $H_2O_2$ in culture medium. After the toxic insult, the medium is replaced by fresh culture medium and cultured in a medium composed by DMEM containing 10% fetal bovine serum and antibiotics at 37° C.

In a next step, in the coculturing situations, ASC or HC016 cells were included seeded in a Boyden chamber (inserts of transwell chamber) as corresponds to the experimental groups explained above.

Up to a period of 24 and 48 h, oligodendroglial viability is quantified by tripan blue exclusion method.

The growth rate (GR) of live cells is calculated as: % live cells-% death cells. Growth rate of oxidized HOG with respect to normal HOG is calculates as: $GR_{oxidized}$ HOG/$GR_{control}$ HOG The resulting values are normalized with respect to oxidized HOG and are represented as percentages in bar graphs.

Results

Figure 7:
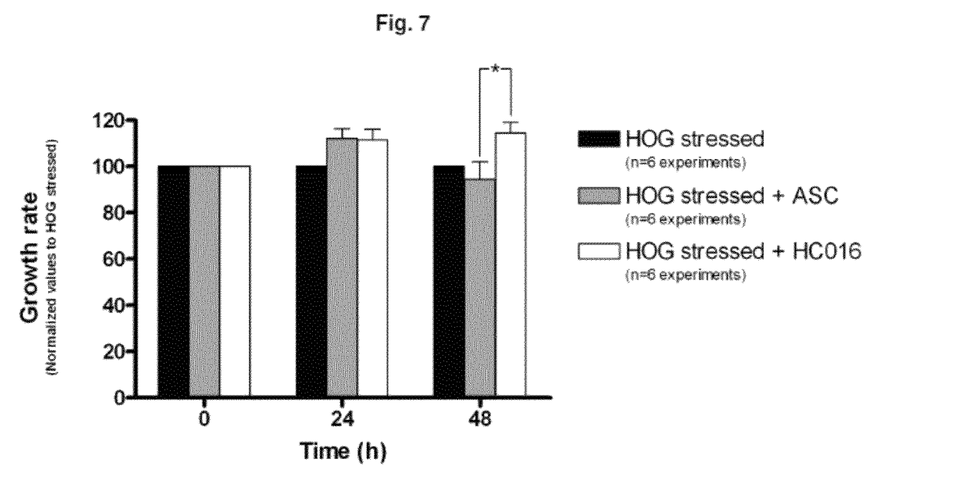
FIG. 7. Neural lineage HOG cells growth rate after oxidative stress insult and effect of ASC and HC016 application on this growth rate. Co-culture of HOG cells stressed with an oxidative environment together with ASC and HC016 increases HOG cells survival. Nonetheless, only co-culture with HC016 sustains this protective effect 48 hours after exposure of HOG cells to the oxidative environment. Asterisk indicates significative statistical difference according to a t-Student test ($p<0.05$) (Example 9).

After 48 hours of oxidative stimulation over HOG cells, the cells co-cultured with HC016 cells, have a normalized growth rate with respect to oxidized HOG 21% higher (FIG. 7) with respect with the HOG cells co-cultured with ASC. While at 24 h both cell types promote the viability of oxidized HOG (FIG. 7) at similar way, at medium term the HC016 cells have a more lasting effect on oxidized HOG. For this reason, the application of these cells as in vitro cell therapy present more benefit with respect to conventional ASC therapy, as HC016 cells let an improvement and increase of the effect over time, related to ASC, over other cell types under stress conditions, as occurs in tissue damage in diseases referred to in this document.

Example 10

Migration Capacity of HC016 Cells Towards Inflammation/Oxidative Stress Signalling Cells Experimental groups consist of control oligodendroglial cells without any modification in the normal culture procedure, oligodendroglial cells cultured in an oxidant environment, coculture of ASC with oligodendroglial cells cultured in an oxidant environment and coculture of HC016 cells with oligodendroglial cells cultured in an oxidant environment To analyze the migration capacity of ASC and HC016 cells, an oxidative stress model is generated with test mammal cells (oligodendroglial cells) whose proliferation and viability is sensitive upon oxidative stress conditions. The oxidative stress model consist of oligodendroglial HOG cells plated and adhered to the bottom of a 24-well plate and cultured in an oxidant environment for 1 hour by adding 0.5 ml of 0.5 mM of $H_2O_2$ to culture medium. After the toxic insult, the medium is replaced with fresh culture medium and cultured with a medium composed of, DMEM containing 10% fetal bovine serum and antibiotics at $37^2$C.

In a next step, in the coculturing situations, ASC or HC016 cells were included seeded in a Boyden chamber (inserts of transwell chamber) as corresponds to the experimental groups explained above.

Up to a period of 24, 48 and 72 hours, transwell inserts are washed in PBS 1× and fixed with 4% formaldehyde in PBS 1× for 12 minutes. Cells on the upper surface of the transwell membrane are removed with the cotton swab of a Q-tip and remaining cells are stained with a 0.1% solution of cresyl violet for 1 hour at room temperature. Then, thoroughly washed in PBS 1× and finally cut from the inserts, mounted flat on glass slides covered with a thin layer of DPX mountant medium (Sigma-Aldrich; Ref. 44581), and visualized under the miscroscope. The membranes are observed under the microscope, representative images of each situation are acquire and the number of cells per area is directly counted for each experimental group.

The quantification is expressed in migrated number of cells per $mm^2$.

Results

We analyzed a total of 10 fields of 0.57 mm2 each (FIG. 8) for a total of 5.7 $mm^2$. In this area, at 48 and 72 hours, HC016 cells have a migratory capacity 32.75 times (3.275%) and 20.61 times (2061%) higher (FIG. 8) with respect to ASC toward the area of damaged cells by oxidative stress. In conclusion, HC016 cells treatment generates a significative stronger and superior chemotactic ability toward HOG cells damaged by extracellular $H_2O_2$, with respect to ASC. The chemotaxis effect that can exert HOG cells after application of $H_2O_2$ may be related to phenomena such as oxidative stress and induction of components of inflammation that occurs after a release of reactive oxygen metabolites.

Example 11

HC016 Cells Pharmaceutic Composition Manufacture

HC016 cells were prepared according to the pharmaceutical formulation which leads to the cell therapy medicinal product for its use in the animal model and determination of its efficacy:

Thus, once carried out the treatment to obtain HC016 cells from the ASC, as specified in Example 2, the cells are disposed in non-pyrogenic glass vials.

For this purpose, HC016 cells are detached from the culture flask by applying a solution of 0.05% trypsin-EDTA, the enzyme activity is neutralized by adding FBS (Biochrom), and centrifugation at 400 g is conducted for cell suspension obtaining. The supernatant is removed, the cell pellet resuspended in saline (Grifols) and a new centrifugation is carried out to remove any traces of previous solutions. The supernatant is discarded and cells are resuspended in an injectable solution (Ringer-Lactate 95% (Grifols) and 5% human albumin (CSL-Behring). We performed cell count and viability analysis using a haemocytometer, and the cell solution was adjusted to a concentration of 200,000 cells/μl.

The pharmaceutical formulation for stereotaxic injection in the animal model is composed of: a solution of 50 μl of HC016 viable cells at a concentration of 200,000 cells/μl in 95% of Ringer-Lactate (Grifols) and 5% human albumin (CSL-Behring), placed in glass vials, sterile and non-pyrogenic (Sword Scientific).

Example 12

Capacity of Protection and/or Functional Motor Rehabilitation of a Cell Therapy Based on the Application of HC016 Cells in an Animal Model of Spinal Cord Injury The experimental groups consist of three groups of 10 adult Sprague-Dawley rats of 250-300 grams of weight. To these animals, under general anesthesia with isoflurane 3-4% a laminectomy was carried out at thoracic level so the spinal cord is exposed. On the dorsal spinal cord a moderate spinal cord injury is applicated by calibrated and defined contusion by a set of parameters such as distance and weight loaded onto a metal plunger of known diameter. The first group of 10 animals received a injury and no therapy at all. The second group of 10 animals received a injury and are treated with ASC-based cell therapy. The third group of 10 animals received injury and are treated with HC016-based cell therapy. Cell therapies, ASC and HC016, are applied 48 hours after injury by stereotaxic injection at 6 points in the spinal levels above and below the injury. Each injection consist of 1 ml of saline containing 200,000 cells, making a total dose of 1,200,000 cells per animal. Rats are supervised at all times in an animal facility and given food and drink ad libitum. The capacity of protection and/or functional motor rehabilitation in each group is determined by a functional test after 1, 2, 3, 4, 6 and 8 weeks exploring locomotion in open field. This test is known as Basso-Beattie-Bresnahan (BBB score) and is a reliable and sensitive method that achieves a score of 21 and provides a semiquantitative measure of recovery in the short, medium and long term (Basso, Beattie and Bresnahan, 1995. A sensitive and reliable locomotor rating scale for open field testing in rats. J Neurotrauma 12, 1-21).

Quantification is expressed as statistical mean of the BBB scale value of each experimental group at each time of exploration.

Results

Figure 9:
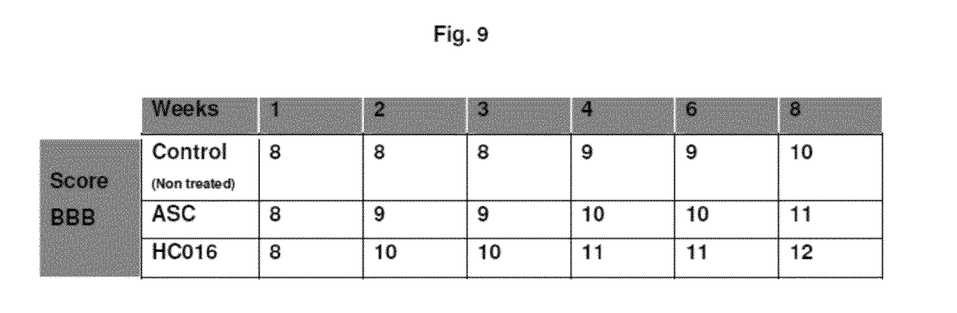
FIG. 9. Table of the evolution of the BBB score (Basso-Beattie-Bresnahan) of three experimental groups of rats with a spinal cord injury consisting of, non-treated rats, treated with ASC and treated with HC016 (Example 12).

The application of HC016 cell-based therapy after spinal cord injury promotes the recovery of motor skills tested on the BBB test. According to the scale of this test, the values indicate that this recovery is at least one point above the conventional therapy based on ASC at all times examined, 1, 2, 3, 4, 6 and 8 weeks after injury (FIG. 9). The evolution of recovery shows that HC016 cells therapy shortens the time to obtain the best score, obtained in the eighth week with HC016 cells.

The invention claimed is:

1. A method of preconditioning mesenchymal stem cells, comprising culturing isolated mesenchymal stem cells in a treatment medium comprising an oxidizing agent, wherein said culturing of the cells in the treatment medium comprises two consecutive treatment cycles of 48-72 hours, followed by a third pre-conditioning cycle of 24-48 hours.

2. The method according to claim 1, wherein the isolated mesenchymal stem cells are from adipose tissue, bone marrow, umbilical cord and/or placenta.

3. The method according to claim 2, wherein the isolated mesenchymal cells are from human adipose tissue.

4. The method according to claim 1, wherein the oxidizing agent is selected from the group consisting of: hydrogen peroxide ($H_2O_2$), calcium peroxide ($CaO_2$), magnesium peroxide ($MgO_2$), zinc peroxide ($ZnO_2$), manganese peroxide ($MnO_2$), plumb peroxide ($PbO_2$) and nitric oxide (NO), nitrous oxide ($N_2O$), ozone ($O_3$), sodium perborate ($NaBO_3$), selenium dioxide ($SeO_2$), silver oxide ($Ag_2O$), ferric chloride ($FeCl_3$), copper salts such as sodium percarbonate ($2Na_2CO_3$), potassium permanganate ($K_2Mn_2O_8$), potassium dichromate ($K_2Cr_2O_7$), lithium, sodium and calcium salts of hypochlorous acid (HClO—), sodium chlorite ($NaClO_2$), chloric acid ($HClO_3$), potassium chlorate ($KClO_3$), aluminium hydroxide ($Al_2O_3$), aluminium hydroxide coprecipitated with magnesium carbonate ($MgCO_3$), arsenic trioxide ($As(OH)_3$), benzoyl peroxide (($C_6H_5CO)_2O_2$), calcium hydroxide ($Ca(OH)_2$), chlordiazepoxide hydrochloride, cupric oxide (CuO), iron oxides, magnesium oxide (MgO), magnesium dioxide, magnesium hydroxide ($Mg(OH)_2$), potassium hydroxide (KOH), sodium hydroxide (NaOH), titanium oxide ($TiO_2$) and/or zinc oxide (ZnO).

5. The method according to claim 4, wherein said culturing of the cells in the treatment medium comprises the following steps:
  a) first cycle: seeding the cells in a culture surface and allowing a conditioning time of between 4 and 8 hours for the cells to adhere and acquire their typical morphology;
  b) adding the treatment medium until reaching a final $H_2O_2$ concentration of between 0.01-0.05 mM;
  c) maintaining for 48-72 hours inside the incubator at 37° C. and 5% $CO_2$ atmosphere;
  d) second cycle: refreshing the treatment medium until reaching again a final $H_2O_2$ concentration of between 0.01-0.05 mM;
  e) incubating these cells for 48-72 hours at 37° C. with 5% $CO_2$;
  f) third cycle: refreshing the treatment medium by applying again said medium until reaching once more a final $H_2O_2$ concentration of between 0.01-0.05 mM; and
  g) incubating these cells for 24-48 hours at 37° C. with 5% $CO_2$.

6. The method according to claim 5, wherein the treatment medium used in steps b), d) and f) comprises conventional cell culture medium at 85-95%, fetal calf serum at 5-15%, antibiotics at 0.5-5% and hydrogen peroxide at 0.01-0.05 mM.

7. Preconditioned mesenchymal stem cells, obtained by a method comprising:
  culturing isolated mesenchymal stem cells in a treatment medium comprising an oxidizing agent, wherein said culturing of the cells in the treatment medium comprises two consecutive treatment cycles of 48-72 hours, followed by a third pre-conditioning cycle of 24-48 hours.

8. The preconditioned mesenchymal stem cells according to claim 7, wherein the cells exhibit an increase in SOD1 gene expression of at least 30% with respect to non treated adipose tissue-derived mesenchymal stem cells (ASC), as measured by a PCR method.

9. The preconditioned mesenchymal stem cells according to claim 8, wherein the cells exhibit an increase in SOD2 gene expression of at least 25% with respect to non treated ASC, as measured by a PCR method.

10. The preconditioned mesenchymal stem cells according to claim 9, wherein the cells exhibit an increase in SOD3 gene expression of at least 50% with respect to non treated ASC, as measured by a PCR method.

11. The preconditioned mesenchymal stem cells according to claim 10, wherein the cells present an increase in Cat gene expression of at least 50% with respect to non treated ASC, as measured by a PCR method.

12. The preconditioned mesenchymal stem cells according to claim 11, wherein the cells exhibit an intracellular increase in GSH of at least of 8% with respect to non treated ASC, as measured by a Tietze enzymatic method.

13. The preconditioned mesenchymal stem cells according to claim 12, wherein the cells exhibit a decrease in intracellular levels of reactive oxygen metabolites (MROs) of at least 10% with respect to non treated ASC, as measured by a fluorometric quantitative method with a DCFA probe.

14. The preconditioned mesenchymal stem cells according to claim 13, wherein the cells exhibit an increase in beta-actin of at least 40% with respect to non treated ASC, as measured by a PCR method.

15. The preconditioned mesenchymal stem cells according to claim 14, wherein the cells exhibit an increase in IGF-1 of at least 40% with respect to non treated ASC, as measured by a PCR method.

16. The preconditioned mesenchymal cells according to claim 7, wherein the isolated mesenchymal cells are from adipose tissue, bone marrow, umbilical cord and/or placenta.

17. The preconditioned mesenchymal cells according to claim 16, wherein the isolated mesenchymal cells are from human adipose tissue.

18. The preconditioned mesenchymal cells according to claim 7, wherein the oxidizing agent is selected from the group consisting of: hydrogen peroxide ($H_2O_2$), calcium peroxide ($CaO_2$), magnesium peroxide ($MgO_2$), zinc peroxide ($ZnO_2$), manganese peroxide ($MnO_2$), lead peroxide ($PbO_2$) and nitric oxide (NO), nitrous oxide ($N_2O$), ozone ($O_3$), sodium perborate ($NaBO_3$), selenium dioxide ($SeO_2$), silver oxide ($Ag_2O$), ferric chloride ($FeCl_3$), sodium percarbonate ($2Na_2CO_3$), potassium permanganate ($K_2Mn_2O_8$), dichromates such as potassium dichromate ($K_2Cr_2O_7$), lithium, sodium and calcium salts of hypochlorous acid (HClO—), sodium chlorite ($NaClO_2$), chloric acid ($HClO_3$), potassium chlorate ($KClO_3$), aluminium hydroxide ($Al_2O_3$), aluminium hydroxide coprecipitated with magnesium carbonate ($MgCO_3$), arsenic trioxide ($As(OH)_3$), benzoyl peroxide (($C_6H_5CO)_2O_2$), calcium hydroxide ($Ca(OH)_2$), chlordiazepoxide hydrochloride, cupric oxide (CuO), iron oxides, magnesium oxide (MgO), magnesium dioxide, magnesium hydroxide ($Mg(OH)_2$), potassium hydroxide (KOH), sodium hydroxide (NaOH), titanium oxide ($TiO_2$) and/or zinc oxide (ZnO).

19. The preconditioned mesenchymal cells according to claim 18, wherein the culturing of the cells in the treatment medium comprises the following steps:
   a) first cycle: seeding the cells in a culture surface and allowing a conditioning time of between 4 and 8 hours for the cells to adhere and acquire their typical morphology;
   b) adding the treatment medium until reaching a final $H_2O_2$ concentration of between 0.01-0.05 mM;
   c) maintaining the cells for 48-72 hours inside the incubator at 37° C. and 5% $CO_2$ atmosphere;
   d) second cycle: refreshing the treatment medium until reaching again a final $H_2O_2$ concentration of between 0.01-0.05 mM;
   e) incubating these cells for 48-72 hours at 37° C. with 5% $CO_2$;
   f) third cycle: refreshing the treatment medium by applying again said medium until reaching once more a final $H_2O_2$ concentration of between 0.01-0.05 mM; and
   g) incubating these cells for 24-48 hours at 37° C. with 5% $CO_2$.

20. The preconditioned mesenchymal cells according to claim 19, wherein the treatment medium used in steps b), d) and f) comprises conventional cell culture medium at 85-95%, fetal calf serum at 5-15%, antibiotics at 0.5-5% and hydrogen peroxide at 0.01-0.05 mM.

* * * * *